United States Patent [19]

Celli

[11] 4,092,362

[45] May 30, 1978

[54] PROCESS FOR THE PREPARATION OF 2-N-PENTYL-3-(2-OXOPROPYL)-1-CYCLOPENTANONE

[76] Inventor: Charles Celli, 70 rue d'Enghein, Eaubonne, France

[21] Appl. No.: 749,691

[22] Filed: Dec. 13, 1976

Related U.S. Application Data

[62] Division of Ser. No. 283,078, Aug. 23, 1972, abandoned.

[30] Foreign Application Priority Data

Sep. 1, 1971 France ................................ 71.31578

[51] Int. Cl.[2] ................................................ C07C 45/00

[52] U.S. Cl. ................................ 260/586 R; 252/522; 560/122

[58] Field of Search ........... 260/586 R, 514 K, 468 K

[56] References Cited

U.S. PATENT DOCUMENTS

| | | | |
|---|---|---|---|
| 3,941,828 | 3/1976 | Buchi | 260/586 R |
| 3,954,834 | 5/1976 | Cohen | 260/586 R |
| 3,981,891 | 9/1976 | Celli et al. | 260/586 R |

*Primary Examiner*—Norman Morgenstern

*Attorney, Agent, or Firm*—Wallenstein, Spangenberg, Hattis & Strampel

[57] ABSTRACT

The valuable odoriferous material 2-n-pentyl-3-(2-oxo-propyl)-1-cyclopentanone is prepared by a process which comprises hydrolysing and decarboxylating a compound of the formula

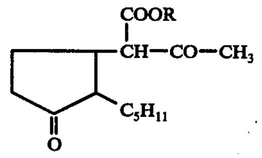

I wherein R represents a hydrocarbyl group, with water under pressure and in an initially substantially neutral medium. The use of 2-n-pentyl-3-(2-oxopropyl)-1-cyclopentanone as an odorant is also disclosed.

6 Claims, No Drawings

PROCESS FOR THE PREPARATION OF 2-N-PENTYL-3-(2-OXOPROPYL)-1-CYCLOPENTANONE

This is a division, of application Ser. No. 283,078, filed Aug. 23, 1972 now abandoned.

This invention relates to a process for the production of the known substance 2-n-pentyl-3-(2-oxopropyl)-1-cyclopentanone and also to perfume formulations containing said substance.

2-n-pentyl-3-(2-oxopropyl)-1-cyclopentanone has now been found to be a valuable odoriferous substance possessing a particularly fragrant magnolia-like aroma.

According to the present invention there is provided a process for the production of 2-n-pentyl-3-(2-oxopropyl)-1-cyclopentanone, which comprises hydrolysing and decarboxylating a compound of the formula

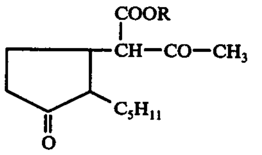

I wherein R represents a hydrocarbyl group, with water, under pressure and in an initially substantially neutral medium.

Pure stereoisomers may be obtained from mixtures of isomers by conventional separation methods.

The hydrolysis and decarboxylation is conveniently carried out at a temperature of from 120° to 300°, preferably from 140° to 250°.

The reaction is conveniently effected using the same weight of water as of 2-n-pentyl-3-(2-oxopropyl)-1-cyclopentanone. The reaction is normally effected in an autoclave from which the air is first purged.

This hydrolysis and decarboxylation under substantially neutral conditions gives the desired product in a good yield, as opposed to the hydrolysis effected in acid and alkaline media, which gives products derived by an intramolecular condensation reaction.

The starting substance of formula

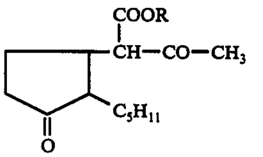

I wherein R represents a hydrocarbyl group, may be prepared by condensing 2-n-pentyl-1-cyclopent-2-en-1-one with a keto ester of the formula:

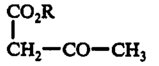

II

The reaction conditions for this step are those of a conventional Michael condensation. The group R is conveniently an alkyl group and preferably a lower alkyl group having from 1 to 5 carbon atoms, for example methyl or ethyl. 2-n-pentyl-3-(2-oxopropyl)-1-cyclopentanone and its stereoisomers have a very strong odour of magnolia showing the remarkable properties of both fixing and magnifying floral odours. Thus, the compound can be used for the preparation of perfumes as well as for the preparation of perfumed products, for example solid and liquid detergents, synthetic washing agents, aerosols or cosmetic products of all kinds. The odorant compositions of this invention may conveniently contain from 1 to 20% by weight, preferably, from 5 to 10% by weight, of 2-n-pentyl-3-(2-oxopropyl)-1-cyclopentanone.

This invention will now be illustrated with reference to the following Examples.

EXAMPLE 1

(a) One liter of absolute ethanol was introduced into a 4 liter flask. 23 g of sodium were added to it. 650 g of ethyl acetoacetate were added to the resulting sodium ethylate solution, then 456 g of 2-n-pentyl-cyclopent-2-en-1-one were added dropwise over one hour. The solution thus obtained was heated over a period of two hours up to the reflux temperature (87° C), held at this temperature for three hours, then allowed to cool and stand at the ambient temperature for 16 hours. The resulting product was neutralised with 65 g of acetic acid and subsequently poured onto 3,300 ml of a 10% aqueous sodium chloride solution. The aqueous layer was then decantated off and extracted three times with the aid of 300 ml of toluene. The toluene extracts were washed to neutrality, the toluene was removed by distillation and the remainder fractionally distilled. There was thus obtained 513 g of 2-n-pentyl-3-(1-carbethoxy-2-oxopropyl)-1-cyclopentanone. Yield = 60%.

(b) 513 g of 2-n-pentyl-3-(1-carbethoxy-2-oxopropyl)-1-cyclopentanone were mixed in an autoclave with an equal weight of water. The autoclave was then purged of the air which it contained, closed and heated up to a temperature of 140°–150° C for 2 hours. After cooling, extraction, washing and distillation, there was obtained 332 g of 2-n-pentyl-3-(2-oxopropyl)-1-cyclopentanone (yield = 90.6%) having $n_D^{20}$ = 1.432 and $d_4^{20}$ = 0.961.

EXAMPLE 2

(a) 750 ml of absolute methanol was introduced into a 2 liter flask. 17.3 g of sodium were added thereto. 580 g of methyl acetoacetate and 456 g of 2-pentyl-cyclopent-2-en-1-one were then added and the mixture was allowed to stand for 48 hours at the ambient temperature. The reaction product was neutralised with 45 g of acetic acid and then poured into 3 liters of a 10% aqueous sodium chloride solution. The product was then worked up as described in Example 1 (a). There were thus obtained 567 g (yield = 70%) of 2-n-pentyl-(1-carbomethoxy-2-oxopropyl)-1-cyclopentanone having: $n_D^{20}$ = 1.4702, $d_4^{20}$ = 1.0545.

(b) 567 g of 2-n-pentyl-(1-carbomethoxy-2-oxopropyl)-1-cyclopentanone were hydrolysed using an equal weight of water according to the method described in Example 1 (b). There were obtained 391 g of 2-n-pentyl-3-(2-oxopropyl)-1-cyclopentanone (overall yield = 80% based on the amount of 2-n-pentyl-cyclopent-2-en-1-one consumed) having the physical constants shown in Example 1 (b).

EXAMPLE 3

A perfumery composition containing 2-n-pentyl-3-(2-oxopropyl)-1-cyclopentanone was prepared as follows:

| | |
|---|---|
| Bergamotte peel Oil Extra | 60 |

-continued

| | |
|---|---|
| Benzyl acetate | 140 |
| Phenylethyl alcohol | 150 |
| Jasmine Absolute | 50 |
| Linalol | 50 |
| Methylnonylacetaldehyde C.12, 10% in ethylphthalate (E.P.) | 60 |
| C.11 aldehyde 10% in E.P. | 20 |
| Hydroxydihydrocitronellal | 140 |
| α-Ionone | 20 |
| Geranium Oil Africa | 60 |
| Civet Absolute 10% in E.P. | 10 |
| Hyacinth Absolute | 10 |
| Vetiver Oil Bourbon | 35 |
| Cyclopentadecanolide | 20 |
| Tonka beans absolute | 20 |
| Rose Oil Eastern | 15 |
| Musk ketone | 30 |
| α-Amylcinnamaldehyde | 30 |
| 2-n-pentyl-3-(2-oxo-propyl)-1-cyclopentanone | 80 |
| | 1,000 |

EXAMPLE 4

| -Perfumery composition- | |
|---|---|
| Bergamotte Oil | 100 |
| Lemon Oil | 40 |
| Lavender Oil | 50 |
| Galbanum Oil 10% in E.P. | 100 |
| Patchouli Oil | 30 |
| Ylang-Ylang Extra | 50 |
| Hydroxydihydrocitronnellal | 150 |
| Rose Absolute, Centifolia | 20 |
| Jasmine Absolute | 40 |
| C.11 aldehyde 10% in E.P. | 10 |
| C.12 aldehyde 10% in E.P. | 20 |
| Trimethylundecanal 10% in E.P. | 10 |
| Phenylethyl alcohol | 50 |
| Geraniol | 60 |
| Guaiol acetate | 40 |
| Oak moss absolute | 10 |
| Kephalis | 40 |
| Cyclohexadecanolide | 20 |
| Musk ketone | 30 |
| Coumarin | 30 |

-continued

| -Perfumery composition- | |
|---|---|
| 2-n-pentyl-3-(2-oxo-propyl)-1-cyclopentanone | 100 |
| | 1,000 |

We claim:

1. A process for the production of 2-n-pentyl-3-(2-oxopropyl)-1-cyclopentanone, which comprises hydrolysing and decarboxylating a compound of the formula

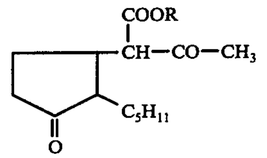

I wherein R represents a hydrocarbyl group, at an elevated temperature and under pressure with water in an initially substantially neutral medium.

2. A process according to claim 1, wherein the reaction is effected at a temperature of 120° to 300° C.

3. A process according to claim 1, wherein the reaction is effected at a temperature of 140° to 260° C.

4. A process according to claim 1, wherein R represents an alkyl group having from 1 to 5 carbon atoms.

5. A process according to claim 1, wherein R represents a methyl or ethyl group.

6. A process according to claim 1, wherein the starting material of formula I, wherein R represents a hydrocarbyl group, is prepared by condensing 2-n-pentylcyclopent-2-en-1-one with a keto ester of the formula

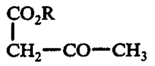

II

* * * * *